US00PP21917P2

(12) United States Plant Patent
Blackman

(10) Patent No.: US PP21,917 P2
(45) Date of Patent: May 10, 2011

(54) ***PENNISETUM* PLANT NAMED 'BURGUNDY BUNNY'**

(50) Latin Name: *Pennisetum alopecuroides*
Varietal Denomination: Burgundy Bunny

(76) Inventor: Lorne Blackman, Walla Walla, WA (US)

( * ) Notice: Subject to any disclaimer, the term of this patent is extended or adjusted under 35 U.S.C. 154(b) by 0 days.

(21) Appl. No.: 12/592,332

(22) Filed: Nov. 24, 2009

(51) Int. Cl.
*A01H 5/00* (2006.01)

(52) U.S. Cl. ..... Plt./384

(58) Field of Classification Search ..... Plt./384
See application file for complete search history.

(56) References Cited

OTHER PUBLICATIONS

*Pennisetum alopecuroides* 'Little Bunny' Miniature Fountain Grass 2009, retrieved on Nov. 30, 2010, retrieved from the Internet at <http://www.magnoliagardensnursery.com/productdescrip/Pennisetum_Little.html> 1 page.*
Floridata #817 *Pennisetum alopecuroides* 2004, retrieved on Nov. 30, 2010, retrieved from the Internet at <http://www.floridata.com/ref/p/penn_alo.cfm> 3 pages.*

* cited by examiner

*Primary Examiner* — June Hwu

(57) ABSTRACT

A new and distinct cultivar of *Pennisetum* plant named 'BURGUNDY BUNNY' that is a warm season grass characterized by compact clumping habit, slow growth, and pronounced dark-red foliage in spring. In combination these traits set 'BURGUNDY BUNNY' apart from all other existing varieties of *Pennisetum* known to the inventor.

2 Drawing Sheets

Genus: *PENNISETUM* Species: *alopecuroides*.
Denomination: 'BURGUNDY BUNNY'.

BACKGROUND OF THE INVENTION

The present invention relates to a new and distinct cultivar of fountain grass grown as an ornamental for garden and landscape. The new invention from the family Poaceae, formerly referred to as Gramineae, is known botanically as *PENNISETUM alopecuroides* and will be referred to hereinafter by the cultivar name 'BURGUNDY BUNNY'.

'BURGUNDY BUNNY' was discovered in 2005 as a naturally occurring individual plant mutation which the inventor discovered growing within his commercial crop of *Pennisetum alopecuroides* 'Little Bunny' (unpatented). The crop of 'Little Bunny' and the discovered mutation were growing in 1 gallon containers which were standing out of doors at the inventor's nursery in Walla Walla, Washington State. The inventor observed that the new variety bore pronounced dark-red foliage and was dense and compact in habit. The closest comparison variety known to the inventor is the parent variety *Pennisetum* 'Little Bunny'. 'BURGUNDY BUNNY' is distinguishable from the comparison plant by foliage color, growth rate, and mature dimensions.

The distinguishing characteristics of 'BURGUNDY BUNNY' include compact clumping habit, small plant dimension, slow growth, and pronounced dark-red foliage beginning in spring. 'BURGUNDY BUNNY' blooms summer through autumn. 'BURGUNDY BUNNY' is a warm season, winter dormant grass. Dimensions the first year are 30 cm in height when in flower, and 20 cm in width. Mature dimensions are 30-35 cm in height when in flower, and 40 cm in width. Cultural requirements include full sun, well-draining porous soil, and moderate water. 'BURGUNDY BUNNY' is hardy in USDA Zone 6.

The first asexual propagation of 'BURGUNDY BUNNY' was accomplished by the inventor, at the inventor's nursery in Walla Walla, Wash. Asexual propagation was conducted in 2006. The method of propagation used was division. Since that time under careful observation 'BURGUNDY BUNNY' has been determined fixed, stable, uniform, and true to type in subsequent generations of asexual propagation.

SUMMARY OF THE INVENTION

The following traits have been repeatedly observed and represent the distinguishing characteristics of 'BURGUNDY BUNNY'. These traits in combination set 'BURGUNDY BUNNY' apart from all other existing varieties of *Pennisetum* known to the inventor. 'BURGUNDY BUNNY' has not been tested under all possible conditions and phenotypic differences may be observed with variations in environmental, climatic, and cultural conditions without however any variance in genotype.

1. 'BURGUNDY BUNNY' exhibits pronounced dark-red foliage beginning in spring.
2. 'BURGUNDY BUNNY' exhibits compact clumping habit.
3. 'BURGUNDY BUNNY' is slow growing.
4. 'BURGUNDY BUNNY' is 30-35 cm. in height when in flower and 40 cm. in width at maturity.
5. 'BURGUNDY BUNNY' performs best in full sun and well-draining porous soil, with moderate water.
6. 'BURGUNDY BUNNY' blooms summer through autumn.
7. 'BURGUNDY BUNNY' is hardy in USDA Zone 6.

BRIEF DESCRIPTION OF THE DRAWINGS

The accompanying color drawings illustrate the overall appearance of 'BURGUNDY BUNNY' showing the color as true as is reasonably possible to obtain in color reproductions of this type. Color in the drawings may differ from color values cited in the detailed botanical description, which accurately describe the actual color of 'BURGUNDY BUNNY'. The plant exhibited in the drawings is 1-year-old and growing out-of-doors.

The drawing labeled

The drawing labeled

BOTANICAL DESCRIPTION OF THE PLANT

Figure 1:
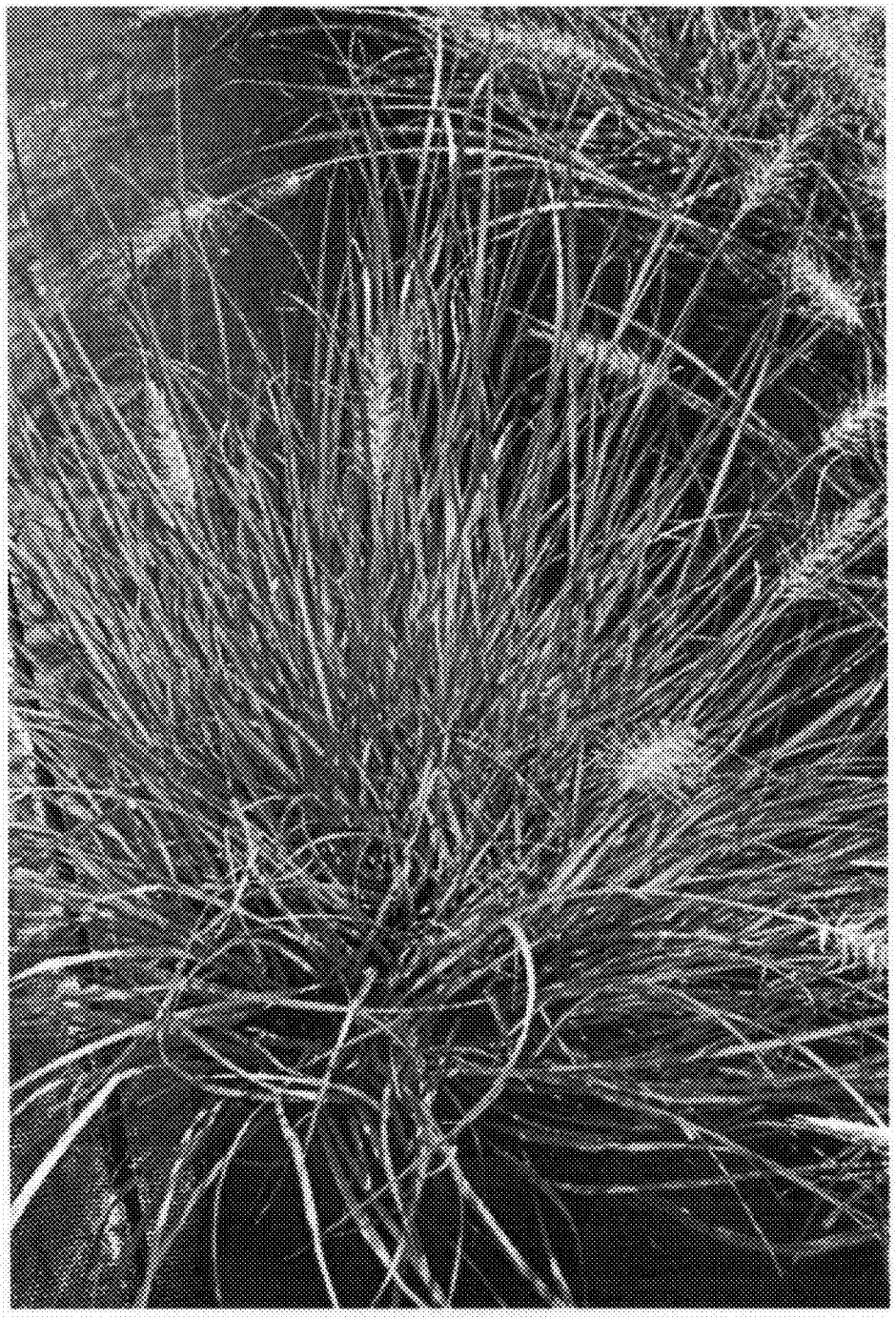
FIG. 1 depicts 'BURGUNDY BUNNY' in bloom growing in a 1-gallon container out-of-doors.
Figure 2:
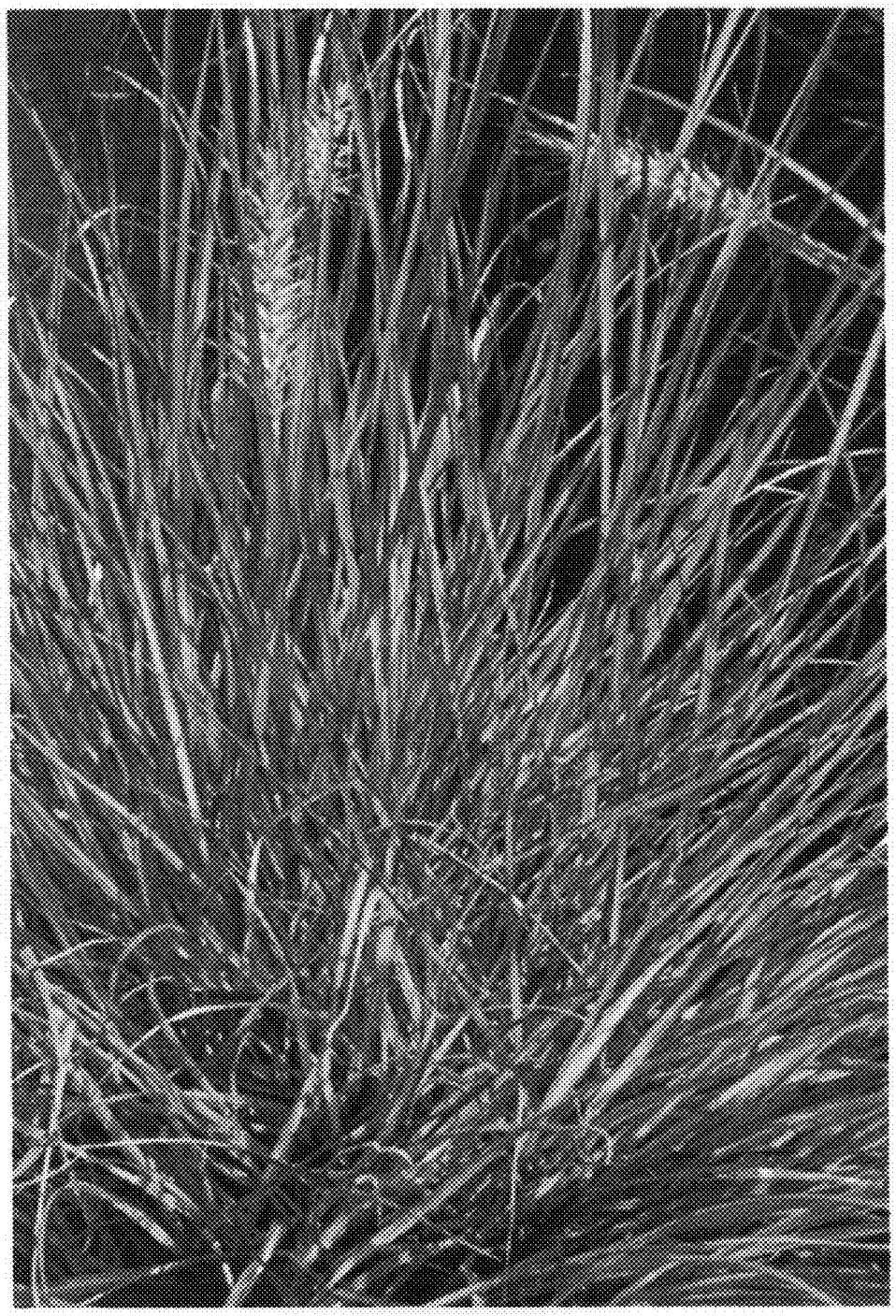
FIG. 2 depicts the habit and foliage color of 'BURGUNDY BUNNY' growing out-of doors in the landscape. The drawings were made in summer using conventional techniques and although flower and foliage color may appear different from actual color due to light reflectance, they are as accurate as possible by conventional photography.

The following is a detailed botanical description of 'BURGUNDY BUNNY'. Observations, measurements, values and comparisons were collected in the month of October 2008 in Arroyo Grande, Calif., from 9-month-old plants growing out-of-doors in 1-liter containers. Color determinations are made in accordance with The 2001 Royal Horticultural Society Colour Chart from London, England, except where general color terms of ordinary dictionary significance are used. The growing requirements of 'BURGUNDY BUNNY' are similar to the species.

Botanical classification: *PENNISETUM alopecuroides* 'BURGUNDY BUNNY'.
Family: Poaceae (formerly referred to as Gramineae).
Genus: *PENNISETUM.*
Species: *alopecuroides.*
Denomination: 'BURGUNDY BUNNY'.
Common name: Fountain grass.
Habit: Compact clumping.
Plant appearance: Tufted and tossled.
Plant shape: Fountain-shaped.
Commercial category: Ornamental grass.
Use: For garden and landscape.
Suggested commercial container size: 1-liter container.
Parentage: *PENNISETUM alopecuroides* 'BURGUNDY BUNNY' was discovered as a sport of the following parent:
*Parent.*—An individual *Pennisetum* 'Little Bunny' (unpatented).
Propagation method: Division.
Rooting system: Fibrous.
Vigor: Low.
Crop time (range): 9-12 months to produce a 1-liter container from stem cuttings.
Temperature (range): The recommended air temperature is 20-21° Centigrade.
Plant dimensions (first year): 30 cm. in height when in flower and 20 cm. in width.
Plant dimensions (at maturity): 30-35 cm. in height when in flower and 40 cm. in width.
Cultural requirements: Grow in full sun and well-draining porous soil, with moderate water.
Pest or disease resistance: None known to the inventor.
Pest or disease susceptibility: None known to the inventor.
Hardiness: USDA Zone 6.
Special considerations: Perennial in frost-free zones.
Culm:
*Length.*—17 cm.
*Width.*—0.20 cm.
*Shape.*—Cylindrical.
*Form.*—Hollow.
*Surface.*—Glabrous.
*Color.*—N144C.
*Node color.*—N144C.
*Node surface.*—Ciliate.
*Node dimensions.*—3 mm. in length and 0.22 cm. in width.
*Internode* (*range*).—9-12 cm.
Foliage:
*Type.*—Winter deciduous.
*Arrangement* (*range*).—Basal to alternate.
*Division.*—Simple.
*Attachment.*—Sheathing.
*Sheath open or closed.*—Partially open.
*Sheath length.*—4.5 cm in length.
*Sheath width.*—0.22 cm.
*Sheath color.*—N144A.
*Sheath surface.*—Fluted.
*Leaf shape.*—Flattened linear. Blade length (average): 22 cm. Blade width (average): 0.25 cm. Blade margin: Scabrous. Blade surface (abaxial and adaxial): Fluted. Blade color (first new growth after winter dormancy, both surfaces): From yellow 2B and 2C to pale yellow green N144B and N144C. All colors are present on an individual plant. Blade color (summer growth phase, both surfaces): All leaves emerge yellow 2B and 2C to pale yellow green N144B and N144C (both surfaces). Blade color becomes bright orange red N34B and N34A beginning from the apex and eventually throughout entire leaf blade. Fully developed leaves age to maroon 187D (adaxial surface) and 187B (abaxial surface). By late summer, all colors cited above are present on an individual plant.
*Leaf apex.*—Cirrhose.
*Leaf base.*—Truncate.
*Venation pattern.*—Parallel.
*Vein color* (*abaxial and adaxial surfaces*).—177A.
*Leaf fragrance.*—None observed.
Inflorescence:
*Type.*—Terminal spike.
*Appearance.*—Plumose.
*Bloom season.*—Summer through autumn.
*Persistent or self-cleaning.*—Self-cleaning.
*Fragrance.*—None observed.
*Lastingness of inflorescence* (*range*).—5-7 days.
*Quantity* (*range*).—18-26 per 1-liter container plant.
*Shape* (*range*).—Cylindrical to narrow oblong.
*Aspect.*—Facing outward and upward.
*Length* (*range*).—6.50 to 7 cm.
*Width* (*range*).—2 to 2.50 cm.
*Color.*—Overall color effect is 158D with underlying glints of 187A and 199D that become apparent in bright sunlight.
*Rachilla.*—Rachilla shape: Sub-cylindrical. Rachilla surface: Minutely warty. Rachilla dimensions (average): <1 mm. in length. Rachilla color: A combination of 187A and 152D.
*Glume.*—Outer glume shape: Lanceolate. Inner glume shape: Lanceolate. Quantity (average): 2 at base of spikelet. Outer glume dimensions: 6 mm. in length and <1.5 mm. in width. Inner glume dimensions. 5 mm. in length and <1 mm. in width. Outer glume color: 199D. Inner glume color: 199D. Glume surface: Glabrous. Glume apex: Acute.
*Floret.*—Arrangement: Arranged in 2 rows. Floret shape: Lanceolate. Floret dimensions (range): 3-4 mm. in length and 2-3 mm. in width. Floret color:

138D. Lemma quantity: 1 per floret. Palea quantity: 1 per floret. Lemma dimensions (average): 9 mm. in length and 6 mm. in width. Palea dimensions (range): 6-1.60 cm. in length and 1 mm. in width. Lemma color: 161D. Palea color: 161D. Awn quantity (average): 5 per floret. Awn color: 199D. Awn dimensions (average): 6 mm. in length and <1 mm. in width.

*Reproductive organs.*—Stamen: 3 in number. Stamen length: 3 mm. Stamen color: 156A. Anther: 3 in number. Anther length: 2.50 mm. Anther color: 200C. Pistil: 1 in number. Pistil color: 156A. Pistil length: 6 mm. Style: 2 in number. Style shape: Plumose. Ovary: 146D. Ovary: Superior, rounded, 1 mm in diameter. Seed: Seed has not been found to be present during repeated observations of the inflorescence.

I claim:

1. A new and distinct cultivar of *Pennisetum* plant named 'BURGUNDY BUNNY' as described and illustrated herein.

* * * * *